US007153504B2

(12) United States Patent
Follette et al.

(10) Patent No.: US 7,153,504 B2
(45) Date of Patent: Dec. 26, 2006

(54) STABILIZED PANCREAS PRODUCT

(75) Inventors: Andrew J. La Follette, Big Lake, MN (US); Jennifer L.G. van de Ligt, Elk River, MN (US); Christiaan P.A. van de Ligt, Elk River, MN (US); Mark D. Newcomb, Independence, MN (US); W. Michael Craig, Monticello, MN (US); Kevin Touchette, Princeton, MN (US)

(73) Assignee: CAN Technologies, Inc., Minnetonka, MN (US)

( * ) Notice: Subject to any disclaimer, the term of this patent is extended or adjusted under 35 U.S.C. 154(b) by 0 days.

(21) Appl. No.: 10/901,969

(22) Filed: Jul. 30, 2004

(65) Prior Publication Data

US 2006/0024355 A1 Feb. 2, 2006

(51) Int. Cl.
*A61K 38/43* (2006.01)
*A61K 38/54* (2006.01)
*A23K 1/165* (2006.01)

(52) U.S. Cl. .................. 424/94.21; 424/94.1; 424/94.2; 424/442

(58) Field of Classification Search .................... None
See application file for complete search history.

(56) References Cited

U.S. PATENT DOCUMENTS

| | | | |
|---|---|---|---|
| 2,503,313 A | | 4/1950 | Levin |
| 2,710,806 A | | 6/1955 | Paul et al. |
| 2,878,123 A | | 3/1959 | Beuk et al. |
| 3,313,705 A | * | 4/1967 | Constant et al. ......... 424/94.21 |
| 3,493,399 A | | 2/1970 | Levin |
| 3,844,891 A | | 10/1974 | Hess et al. |
| 3,893,992 A | * | 7/1975 | De Benneville ............ 530/323 |
| 3,926,730 A | * | 12/1975 | Huper et al. ................ 435/201 |
| 3,956,483 A | * | 5/1976 | Lewis ..................... 424/94.21 |
| 4,019,958 A | | 4/1977 | Hell et al. |
| 4,029,641 A | | 6/1977 | Hafner et al. |
| 4,088,539 A | | 5/1978 | Muller |
| 4,280,971 A | | 7/1981 | Wischniewski et al. |
| 4,447,412 A | | 5/1984 | Bilton |
| 4,797,287 A | | 1/1989 | Pich et al. |
| 5,112,624 A | * | 5/1992 | Johna et al. .................... 426/2 |
| 5,378,462 A | | 1/1995 | Boedecker et al. |
| 5,674,532 A | | 10/1997 | Atzl et al. |
| 5,753,223 A | | 5/1998 | Shibahara et al. |
| 5,858,357 A | * | 1/1999 | Trnka et al. ............. 424/94.64 |
| 5,861,177 A | * | 1/1999 | Atzl et al. ................... 424/489 |
| 5,861,291 A | * | 1/1999 | Abboudi et al. ............ 435/183 |
| 5,902,617 A | | 5/1999 | Pabst |
| 5,993,806 A | * | 11/1999 | Galle ........................ 424/94.3 |
| 6,440,448 B1 | | 8/2002 | Intelisano |
| 6,676,933 B1 | | 1/2004 | Vergez et al. |

FOREIGN PATENT DOCUMENTS

EP  0 115 023 B1  7/1988

OTHER PUBLICATIONS

Thomas CL, ed. 1997. Taber's Cyclopedic Medical Dictionary, 18th ed. pp. 1394-1395.*
Olson W. NACMO News [online article; accessed Jul. 6, 2005]. 3 pages.*
Scharpe S et al. 1997. Pancreatic enzyme replacement. In Pharmaceutical Enzymes, Lauwers et al., eds.; vol. 84, pp. 208-209.*
Cortamira, et al., "Pancreatic extract used as additive in weaning piglet diets", Digestive Physiology in Pigs Proceedings of the 7th Inter, 88: 483-486 (1997).
Owsley, et al., "Effects of age and diet on the development of the pancreas and the synthesis and secretion of pancreatic enzymes in the young pig", *J. Anim. Sci.*, 63(2): 497-504 (Aug. 1986), on-line abstract only dated Mar. 16, 2004.
Mahan, et al., "Effect of pig weaning weight and associated nursery feeding programs on subsequent performance to 105 kilograms body weight", *J. Anim. Sci.*, 69(4): 1370-8 (Apr. 1991); on-line abstract only dated Mar. 16, 2004.
Efird, et al., "The development of digestive capacity in young pigs: effects of age and weaning system", *J. Anim. Sci.*, 55(6): 1380-7 (Dec. 1982) ; on-line abstract only dated Mar. 16, 2004.
Pierzynowski, et al., "Development of exocrine pancreas function in chronically cannulated pigs during 1-13 weeks of postnatal life", *J. Pediatr. Gastroenterol Nutr.*, 10(2): 206-12 (Feb. 1990); on-line abstract only dated Mar. 16, 2004.
Pierzynowski, et al., "Development and regulation of porcine pancreatic function", *Int. J. Pancreatol.*, 18(2): 81-94 (Oct. 1995); on-line abstract only dated Mar. 16, 2004.
McCracken, et al., "Diet-dependent and diet-independent metabolic responses underlie growth stasis of pigs at weaning", *J. Nutr.*, 125(11): 2838-45 (Nov. 1995); on-line abstract only dated Mar. 16, 2004.
Lindemann, et al., "Effect of age, weaning and diet on digestive enzyme levels in the piglet", *J. Anim. Sci.*, 62(5): 1298-307 (May 1986); on-line abstract only dated Mar. 16, 2004.
Etheridge, et al., "The effect of diet on performance, digestability, blood composition and intestinal microflora of weaned pigs", *J. Anim. Sci.*, 58(6): 1396-402 (Jun. 1984); on-line abstract only dated Mar. 16, 2004.
Le Drean, et al., "Comparison of the kinetics of pancreatic secretion and gut regulatory peptides in the plasma of preruminant calves fed milk or soybean protein", *J. Dairy Sci.*, 81(5): 1313-21 (May 1998); on-line abstract only dated Mar. 18, 2004.

(Continued)

Primary Examiner—Sandra E. Saucier
Assistant Examiner—Lora E Barnhart
(74) Attorney, Agent, or Firm—Foley & Lardner, LLP

(57) ABSTRACT

The present invention provides stabilized pancreas products useful, for example, as an animal feed additives. The invention also provides for feed additives and feed rations comprising a stabilized pancreas product. Further, the invention provides for methods of making stabilized pancreas products. The present invention also provides for methods of supplementing an animal feed utilizing stabilized pancreas products.

36 Claims, No Drawings

OTHER PUBLICATIONS

Lopez-Palomo, et al., "Regulation by diet of the pancreas enzyme content of suckling goats", *Arch. Physiol. Biochem.,* 105(6): 566-71 (Oct. 1997); on-line abstract only dated Mar. 18, 2004.

"Digestive Tract Changes", Tri-State Swine Nutrition Guide, *Bulletin,* pp. 869-898, on-line Mar. 16, 2004.

Liu, et al., "Exogenous enzymes for pig diets: an overview", *Department of Animal Science, University of Manitoba;* 11 pages; on-line Mar. 16, 2004.

Cera, et al., "Effect of weaning, week postweaning and diet composition on pancreatic and small intestinal luminal lipase response in young swine", *Journal of Animal Science,* 68(2): 384-391 (1990); on-line abstract only dated Mar. 16, 2004.

Marion, et al., "Weaning and Feed Intake Alter Pancreatic Enzyme Activities and Corresponding mRNA Levels in 7-d-Old Piglets", *J Nutr,* 133: 362-368 (2003).

Hedemann, et al., "Exocrine Pancreatic Secretion Is Stimulated in Piglets Fed Fish Oil Compared with Those Fed Coconut Oil or Lard", *J. Nutr.,* 131: 3222-3226 (2001).

Kats, et al., "The Effect of Spray-Dried Porcine Plasma on Growth Performance in the Early-Weaned Pig", *J. Anim. Sci.,* 72: 2075-2081 (1994).

Gestin, et al., "Diet Modifies Elastase I and II Activities and mRNA Levels during Postnatal Development and Weaning in Piglets", *J. Nutr.,* 127: 2205-2211 (1997).

Rantzer, et al., "Pancreatic Exocrine Secretion During the First Days After Weaning in Pigs", *J. Anim. Sci.,* 75: 1324-1331 (1997).

Jensen, et al., "Development of Digestive Enzymes in Pigs with Emphasis on Lipolytic Activity in the Stomach and Pancreas", *J. Anim. Sci.,* 75: 437-445 (1997).

Gupta, et al., "Lipase assays for conventional and molecular screening: an overview", *Biotechnol. Appl. Biochem,* 37: 63-71 (2003).

Holden, et al., "Iowa State University Life Cycle Swine Nutrition", pp. 1-41.

* cited by examiner

STABILIZED PANCREAS PRODUCT

BACKGROUND OF THE INVENTION

1. Field of the Invention

The present invention provides a stabilized pancreas product, useful, for example, as an animal feed additive.

2. Background of the Invention

Animals encounter periods of suboptimal utilization of feed, for example, during periods of change in production, such as the transition from one feed source or ration to a different food source or ration. These changes often result in the poor utilization of dietary nutrients, and result in less efficient production and increased feed costs.

For example, the swine industry recognizes that nutrition and maximal utilization of feed are important as pigs generally grow much faster in proportion to their body weight than larger animals. See Ensminger, *Animal Science,* 9th Ed. Interstate Publishers, Inc., Danville, Ill. (1991). To promote efficient growth, swine may be fed a high-energy ration which is low in fiber. However, swine differ in the kind and amounts of nutrients needed according to a number of factors including age, function, disease state, nutrient interaction, and environment. See, for example, Hill et al., *Tri-State Swine Nutrition Guide, Bull. No.* 869–98, The Ohio State Univ., Columbus, Ohio (1998); and National Research Council, *Nutrient Requirements of Swine,* 10th Ed., Natl. Acad. Press, Washington, D.C. (1998). To meet these different needs, swine producers may formulate the base feed ration from a wide range of ingredients, including, but not limited to, grain concentrates, protein feeds, pasture, dry forages, silages, and downed crops. In addition, supplements may be used to ensure the ration provides the necessary nutritional requirements. Because each of these ingredients vary in availability, price, and amount or quality of nutrients contained, swine producers change feed ration formulations from time to time. For example, a swine producer may follow a complex schedule of different rations based upon the nutritional needs of each stage of the pig's life, the impact of environmental factors on those nutritional needs, and the availability of specific dietary ingredients.

The weaning transition, that period during which pigs are weaned from the sow onto rations, involves some of the most profound nutritional and environmental changes of any life stage. See, e.g., Efird et al., *J Anim. Sci.* 55:1370 (1982). As a result, growth stasis, commonly referred to as postweaning lag, is frequently observed in weanling pigs. During postweaning lag, pigs may fail to gain, and may even lose, weight. Postweaning lag may cause significant losses in the swine industry where feed costs account for approximately sixty-five to seventy-five percent of total production costs. Swine producers attempt to minimize the period of postweaning lag through the use of specialized food sources and feed supplements, such as plasma and blood-derived protein, milk products, and soy concentrate, to feed weanling pigs in a phase-feeding program. These food sources and supplements are closely tailored to a weanling pig's nutritional needs, and, as such, may significantly increase the cost of the final feed ration. Thus, the weaning period and postweaning lag significantly impact the efficiency and cost of swine production.

Although a large number of environmental stressors may contribute to the duration of the postweaning lag period, predominant factors are believed to be the change in feed form (from sow's milk to ration) and adjustment to new dietary ingredients. See McCracken et al., *J Nutr.* 125:2838 (1995); and Pierzynowski et al., *J. Pediatr. Gastroenterol. Nutr.* 16:287 (1993). During the weaning transition, pigs must adapt from a liquid-based diet consisting of sow's milk to a solid-based diet consisting of formulated animal rations. This change in diet and dietary nutrients, which may occur abruptly, often induces significant physiological responses in weanling pigs, including changes in the morphology of the small intestine and exocrine pancreas function, Cera et al., *J Anim. Sci.* 66:574 (1988); Cera et al., *J. Anim. Sci.* 68:384 (1990), and quantitative and qualitative changes in exocrine pancreas function, Lindemann et al., *J Anim. Sci.* 62:1298 (1986).

Physiology and Function of the Pancreas.

The pancreas is a significant accessory organ of digestion which functions as both an endocrine gland and as an exocrine secretory gland. See, e.g., Currie, *Structure And Function Of Domestic Animals,* Butterworths Pub., Boston, Mass. (1988). Located in the abdominal cavity in the mesentery, the pancreas secretes digestive enzymes which pass through one or more pancreatic ducts to the small intestine. A diverse array of pancreatic enzymes are known, and these enzymes are generally responsible for the hydrolytic processing of dietary nutrients into units capable of being absorbed by the small intestine. The pancreas secretes enzymes capable of processing each of the major nutrient classes—carbohydrates, lipids, and proteins. Examples of enzymes for processing each of these nutrient classes are respectively known as amylases, lipases, and proteases. Levels of pancreatic enzymes quantitatively and qualitatively change throughout the pig's life based upon the amount and composition of a pig's dietary nutrients. Ethridge et al., *J Anim. Sci.* 58:1396 (1984).

In a non-pathogenic state, the pancreatic acini cells produce inactive forms of these digestive enzymes. Such forms are known as zymogens or proenzymes. Inactive digestive enzymes are sequestered within zymogen granules, and are activated by proteolytic cleavage, primarily by the enzyme trypsin, once they are secreted into the small intestine. The activation of trypsin, in turn, is orchestrated by trypsin inhibitors, present in acinar and ductal secretions, and duodenal enterokinase, an enzyme generally only present in portions of the small intestine. The combined affect of this regulation ensures that pancreatic enzymes are activated only where needed to effect the hydrolytic processing of dietary nutrients.

Pancreatic Function During Periods of Major Production Changes.

Several investigators have documented the development of the digestive capability of young pigs and the affect of a pig's age, weight, and ration on exocrine pancreas function. For example, Pierzynowski et. al., *J Pediatr. Gastroenterol Nutr.* 16:287 (1993), reported that the maturation of the exocrine pancreas function is more dependant on weaning than age. Initially, the digestive activity of pancreatic enzymes in weanling pigs is decreased as compared to suckling pigs. However, both basal and postprandial levels of amylases, lipases, proteases, and total pancreatic exocrine secretions increased with time in weanling pigs. These changes correlate strongly with changes in the weanling pig's diet but not with age.

Limits of Exogenous Enzyme Therapy.

Some swine producers have turned to exogenous enzymes as feed additives. The investigation and commercial exploitation of these enzymes has only recently become available through the use of advanced recombinant DNA technology and exogenous expression of enzymes in bacterial and other microbial systems. However, there are several factors limiting the usefulness of exogenous enzymes in animal feed.

First, those skilled in the art have long recognized that exogenous enzymes are not needed to aid digestion in healthy animals. For example, Holden et al., *Life Cycle Swine Nutrition*, PM-489, 17th Rev., Iowa State Univ., Ames, Iowa (2000), states that pigs "produce adequate quantities of digestive enzymes for digestion of the proteins, carbohydrates, and lipids that they are capable of digesting." Instead, those skilled in the art utilize exogenous enzymes in order to aid digestion of substances that animals are intrinsically incapable of digesting. For example, barley contains β-glucans, or water-soluble carbohydrates, which are poorly digested by the pig, and those skilled in the art have recognized that β-glucanase-containing feed rations can aid in the digestion of barley when it is used as a dietary ingredient.

Second, each exogenous enzyme generally targets only a narrow range of substrates. Thus, use of exogenous enzymes to aid the digestion of a feed ration in general would require the complex mixing of feed ration containing specific combinations enzymatic substrates and exogenous enzymes. Such pairing would require a significant knowledge of available exogenous enzyme preparations, their specific substrate specificities, and the proper feed ration formulation and storage conditions. Swine producers using exogenous enzymes for this purpose therefore would have to make detailed ration formulation choices, thereby increasing production costs.

Third, the efficacy of exogenous enzyme preparations is significantly altered during commercial processing and formulation of the feed ration. Commercial processing of animal feed often includes heating, extruding, and pelleting. Aggressive commercial processing of exogenous enzymes substantially destroys enzyme activity. Moreover, exogenous enzymes generally self degrade or catalyze the degradation of feed ingredients once the feed ration is formulated. Both of these events significantly reduce the time over which an enzyme-containing feed ration may be stored.

In addition, the digestive system itself provides a significant challenge to the use of exogenous enzymes as feed additives. The feed of non-ruminant animals, such as pigs, must pass through the highly acidic confines of the stomach where digestion of proteins is initiated. Chyme from the stomach then passes the pylorus into the lumen of the small intestine. Although still highly acidic, chyme is quickly neutralized and made slightly alkaline. As such, the majority of digestive enzymes have pH optima at or above neutrality. Thus, the intrinsic characteristics of the digestive system itself requires that exogenous enzymes remain stable in highly acidic conditions, yet function optimally in slightly alkaline conditions.

Pancreatin.

Pancreatin is a pancreas-derived product that is prepared by drying and hydrolyzing swine pancreas. See, e.g., U.S. Pat. No. 3,956,483 ("Preparing Pancreatin"). Pancreatin is made of dried, defatted pancreas. It is prepared from fresh or fresh-frozen pancreas. Normally the pancreas glands are minced and comminuted with the duodenum, which is added to activate the proteolytic enzymes or zymogens in the pancreas. Alternatively, proteolytic activity is sometimes established in the pancreatin preparation by the addition of active trypsin. The blend then undergoes activation of the enzymes. Thereafter, the pancreas is degreased and dried, generally by vacuum drying at room temperature.

Pancreatin has been used in the animal industry primarily to treat digestive disturbances. See, e.g., U.S. Pat. No. 5,112,624 ("Prevention of digestive disturbances in herbivores"); see also Russian Patent No. 829,115 ("Gastrointestinal disorder in calves"). Pancreatin also has been proposed as a feed additive. For example, Cortamira et al., *Proc. of the 7th Int. Symp. on Digestive Physiology in Pigs*, Univ. Alberta, Edmonton, Alberta (1997), investigated the use of 0.01 to 0.03 percent processed pancreatin in swine feed. See also U.S. Pat. No. 2,878,123 ("Use of Proteolytic Enzymes in Poultry Feed").

Heretofore there has not been a practicable feed additive based on a stabilized pancreas product. For example, U.S. Pat. No. 3,313,705 discloses a low-temperature process for making a lyophilized pancreas-based medicament. See col. 1, lines 65 to 69. However, the process is cumbersome and impractical to replicate on a commercial scale for animal feed. See col. 2, lines 16–51. Additionally, the disclosed product undergoes autolysis under atmospheric conditions and requires special storage procedures (e.g., the use of a dehydrating stopper). See col. 3, lines 27–39.

Therefore, a strong need exists for a practicable stabilized pancreas product that can be used, for example, as a feed additive.

SUMMARY OF THE INVENTION

The present invention relates to stabilized pancreas products, feed additives comprising stabilized pancreas products, methods for producing, and methods of using stabilized pancreas products. In one embodiment, the invention relates to a pancreas product comprised of one or more pancreatic enzymes in their zymogen form. In other embodiments, the invention relates to stabilized pancreas products with specific amylase or protease activity. In another embodiment, the invention relates to feed additives comprising stabilized pancreas products. In other embodiments, the invention relates to feed rations comprising a stabilized pancreas product feed additive.

In other embodiments, the present invention is directed to methods of supplementing animal feed rations with stabilized feed products. Some embodiments encompass a method of supplementing animal feed rations with stabilized feed products before, during, and after periods of production change. In some embodiments, the period of production change is transition from a first food source to a second food source, the transition from a liquid to a solid food source, or the weaning of the young animal from the dam.

In other embodiments, the present invention is directed to methods of making stabilized pancreas products. In one embodiment, the present invention provides a method of making a stabilized pancreas product comprising the steps of emulsifying pancreas glands and blending the emulsified pancreas with an acidifier.

In another embodiment, the invention provides a method of making a stabilized pancreas product by mixing emulsified pancreas with a suitable carrier, and extruding the mixture. In yet another embodiment, the invention relates to a method of making a stabilized pancreas product comprising the steps of atomizing emulsified pancreas, and collecting the atomized pancreas.

DETAILED DESCRIPTION OF THE INVENTION

The present invention is based on the surprising and unexpected discovery of a stabilized pancreas product that can be made in bulk quantities, that is simple to store and process, and that is useful, for example, as an animal feed additive to increase the utilization of nutrients in animals undergoing production changes. The present invention is widely applicable to a range of agriculture and food industries, including the aquaculture industry, beef and dairy cattle industries, commercial pet food industry, horse industry, poultry industry, and swine industry.

Stabilized Pancreas Product

One embodiment of the present invention provides a stabilized pancreas product that is useful, for example, as a feed additive. As used herein, "stabilized pancreas product" refers to a composition derived from substantially whole pancreas glands. These glands may be freed of the layers of mesentery or may be substantially freed of the superficial areolar tissue. Alternatively, the glands may be presented as excised without removal of the superficial mesentery tissue and fat. In either case, it is not necessary to remove the lipids from the stabilized pancreas products of the invention.

As used herein, "stabilized" refers to certain qualities of the pancreas product, such as resistance to enzyme degradative hydrolysis, resistance to microbial and fungal spoilage, and resistance to fat oxidation. As such, stabilized pancreas products of the invention are resistant to enzyme degradative hydrolysis, resistant to microbial and fungal spoilage, and resistant to fat oxidation. Accordingly, stabilized pancreas products of the invention remain stable and resist autolysis or degradation upon exposure to air or water. Moreover, because of these qualities, the stabilized pancreas products of the invention do not require removal of fats or lipids or lyophilization.

In one embodiment, a stabilized pancreas product according to the invention comprises pancreas that has not been hydrolyzed, but rather has been processed to stabilize the pancreatic enzymes. A more specific embodiment encompasses a stabilized pancreas product comprising pancreatic enzymes in zymogen form. As used herein, "zymogen" and "zymogen form" refer to the inactive or nearly inactive precursors of an enzyme. Enzymes synthesized as zymogens may be subsequently activated by cleavage of one or more specific peptide bonds. Such cleavage occurs, for instance, when the precursor of the proteolytic enzyme trypsin, trypsinogen, is hydrolyzed by the enzyme enteropeptidase. See, e.g., Berg et al. (Eds.), *Biochemistry,* 5th Ed., W.H. Freeman and Co., N.Y. (2002).

A stabilized pancreas product according to the invention comprises pancreatic enzymes that do not undergo enzymatic degradation during storage. In one embodiment, a stabilized pancreas product retains at least about 75 percent of its original enzyme activity levels. In other embodiments, a stabilized pancreas product retains at least about 80 percent of its original enzyme activity levels; at least about 85 percent of its original enzyme activity levels; at least about 90 percent of its original enzyme activity levels; or at least about 95 percent of its original enzyme activity levels.

In another embodiment, the stabilized pancreas product comprises pancreatic enzymes that do not undergo significant enzymatic degradation during storage over a period of not less than 2 days. In other embodiments, the stabilized pancreas product comprises pancreatic enzymes that do not undergo significant enzymatic degradation during storage over periods of not less than 10 and 30 days respectively. In yet another embodiment, the stabilized pancreas product comprises pancreatic enzymes that do not undergo significant enzymatic degradation during storage over a period of not less than a year.

The stabilized pancreas product of the invention is provided in both wet and dry forms. In one embodiment, the invention is directed to dry stabilized pancreas products. More specific embodiments encompass dry stabilized pancreas products which range from about 1 percent to about 20 percent moisture content. In other embodiments, the invention is directed to wet stabilized pancreas products. More specific embodiments encompass wet stabilized pancreas products which range from about 20 percent to about 95 percent moisture content.

In other embodiments, the stabilized pancreas product comprises a particular activated enzyme profile. As used herein, "activated enzyme profile" refers to the levels of enzymatic activity exhibited by the stabilized pancreas product when the product is appropriately activated. Several pancreatic enzymes may be of interest to those skilled in the art, such as the pancreatic enzyme classes currently listed as approved for use in livestock by the Association of American Feed Control Officials ("AAFCO"). These approved pancreatic enzyme classes include, among others, α-amylase, lipase and trypsin. Those skilled in the art would recognize, for example, protease zymogens may be activated by incubating the stabilized pancreas products with, among other thing, the contents of the small intestine. Other enzymes may be activated as is known in the art. The stabilized pancreas products of the invention may exhibit a variety of activated enzyme profiles. In one embodiment, a stabilized pancreas product exhibits amylase and protease activity.

As used herein, "amylase activity" may be measured using techniques well known in the art, such as those disclosed in Cesca et al., *Clin. Chim. Acta* 26:437–44 (1969), and Von Worthington (Ed.), *Worthington enzyme manual: enzymes and related biochemicals* 399, Worthington Chemicals, Lakewood, N.J. (1993). In brief, one unit of α-amylase activity is equivalent to the amount of enzyme that catalyzes one micromol (1 μM) of glycosidic linkages in one minute under a set of prescribed conditions. In one method, a suitable substrate test may be conducted using PHADEBAS® Amylase test tablets (Pharmacia Diagnostics AB, Uppsala, Sweden) according to the instructions supplied by the manufacturer. First an aliquot of a test sample is diluted in reagent solution. The aliquot is warmed to 37 degrees Celsius and the amylase test tablet is added. The solution is incubated for a prescribed amount of time and the reaction is stopped by the addition of a sodium hydroxide solution. The solution is clarified either by centrifugation or filtration, and its absorbance is measured against a reagent blank. The absorbance of the sample is proportional to its α-amylase activity. Additionally, other techniques and methods for determining amylase activity are well known in the art. Such methods may be used where the amylase activities levels are compared to the enzyme levels of pancreatin and expressed as a percentage.

As used herein, "protease activity" may be measured using techniques well known in the art, such as Gessesse A and B A Gashe, *Biotechnol. Lett.* 19(5):479–81 (1997). One unit of protease activity is equivalent to the amount of enzyme that liberates from the substrate one microgram of phenolic compound, as expressed as tyrosine equivalents, in one minute under a set of prescribed conditions. In one method, samples are activated by incubation with intestinal contents or a suspension of tissue collected from the small intestine. Once activated, samples are extracted in a sodium chloride solution and suitable filtered dilutions are prepared. After the temperatures of the dilutions and test reagents are equilibrated, a solution containing Hammarsten Casin (Merck KGaA, Darmstadt, Germany) is thoroughly mixed with the diluted samples and incubated. After a prescribed period of time, a solution of trichloroacetic acid is added, and the samples continue to be incubated. After incubation, samples are filtered or centrifuged and its absorbance is measured against a reagent blank and a standard curve of L-tyrosine stock solutions. Additionally, other techniques and methods for determining protease activity are well known in the art. Such methods may be used where protease activities levels are compared to the enzyme levels of pancreatin and expressed as a percentage.

Likewise, those skilled in the art may use known assay techniques to compare the enzyme activity level of a particular pancreatic enzyme of interest in the stabilized pancreas product with the enzyme activity level exhibited in pancreatin. The activity levels of trypsin and chymotrypsin may, for example, be compared using the assay protocol disclosed in Erlanger et al., *Arch. Biochem. Biophys.* 95:271–78 (1961). In another embodiment, the lipase activity levels are compared according to the protocols disclosed in I. G. Borlongan, *Chanos Chanos Aquaculture* 89:315–25 (1990), Gupta et al., *Biotechnol. Appl. Biochem.* 37:63–71 (2003), or Jahic et al., *J Biotechnol.* 102:45–53 (2003).

As used herein, pancreatin conforms to the description promulgated by the United States Pharmacopeial Convention, Inc. (Rockville, Md.). An exemplary pancreatin for use as a comparative baseline may, for instance, be obtained from Sigma-Aldrich, Inc. (St. Louis, Mo.), as catalog number P-7545.

One embodiment of the stabilized pancreas product of the invention comprises a particular activated enzyme profile. In some embodiments, the stabilized pancreas products comprise activated enzyme profiles, as compared on a dry matter basis to pancreatin, at least about 0 percent amylase activity, at least about 3 percent amylase activity, at least about 5 percent amylase activity, at least about 10 percent amylase activity, at least about 15 percent amylase activity, at least about 20 percent amylase activity, at least about 60 percent amylase activity, at least about 70 percent amylase activity, at least about 77 percent amylase activity, at least about 80 percent amylase activity, at least about 90 percent amylase activity, at least about 100 percent amylase activity, at least about 105 percent amylase activity, at least about 110 percent amylase activity, or at least about 120 percent amylase activity.

In other embodiments, the stabilized pancreas product of the invention has an activated enzyme profile, as compared on a dry matter basis to pancreatin, of at least about 20 percent protease activity, at least about 30 percent protease activity, at least about 40 percent protease activity, at least about 70 percent protease activity, at least about 80 percent protease activity, at least about 90 percent protease activity, at least about 100 percent protease activity, at least about 110 percent protease activity, at least about 120 percent protease activity, at least about 130 percent protease activity, at least about 140 percent protease activity, at least about 180 percent protease activity, at least about 190 percent protease activity, at least about 200 percent protease activity, at least about 210 percent protease activity, or at least about 220 percent protease activity.

In other embodiments, the stabilized pancreas product of the invention has an activated enzyme profile, as compared on a dry matter basis to pancreatin, of at least about 20 percent lipase activity, at least about 30 percent lipase activity, at least about 40 percent lipase activity, at least about 70 percent lipase activity, at least about 80 percent lipase activity, at least about 90 percent lipase activity, at least about 100 percent lipase activity, at least about 110 percent lipase activity, at least about 120 percent lipase activity, at least about 130 percent lipase activity, at least about 140 percent lipase activity, at least about 180 percent lipase activity, at least about 190 percent lipase activity, at least about 200 percent lipase activity, at least about 210 percent lipase activity, or at least about 220 percent lipase activity.

In other embodiments, the invention includes a stabilized pancreas product having an activated enzyme profile that comprises a combination of any of the foregoing levels of amylase, protease, and lipase activity.

Production of Stabilized Pancreas Product

The invention also includes methods of producing a stabilized pancreas product from animal pancreas glands. In each method, the purpose of processing is to stabilize the pancreatic enzymes, i.e., to protect the resulting product from enzyme degradative hydrolysis, microbial and/or fungal spoilage, and/or fat oxidation. Each of the following production processes provides a different means of stabilizing the pancreas product of the invention.

Animal pancreas glands may be obtained from a variety of sources, such as offal from the slaughter of animals. In one embodiment, pancreas glands are collected from pigs. In another embodiment, pancreas glands are collected from cattle. Those skilled in the art would also recognize that the pancreas glands of many additional animal species are obtainable from animals slaughtered in local abattoirs and slaughterhouses. However, the invention is not limited by the source of the pancreas glands.

In one embodiment, the stabilized pancreas product is produced from emulsified pancreas glands. Pancreas glands may be emulsified by any means known in the art. For example, emulsification may be achieved using a plate grinder or similar instrument, with or without the addition of water. As a result, emulsified pancreas may contain from about 5 percent to about 95 percent dry matter. Those skilled in the art would recognize the dry matter content of the emulsified pancreas may vary according to the production process selected. For example, a spray drying process may require an emulsified pancreas with from about 5 percent to about 50 percent dry matter.

One embodiment of the present invention provides a method of making a stabilized pancreas product using an extrusion process. In brief, emulsified pancreas is blended with a carrier. There are many suitable carriers, for example, the feed ingredients, grains or fiber sources including their respective byproducts. More particularly, suitable carriers include corn and/or soy hulls. Optionally, a fiber source or byproduct thereof, such as hull fiber, cotyledon fiber, bran fiber, vegetable root fiber, or a combination thereof, may also be added to the blend. More particularly, soy hulls may be added to the blend as a fiber source. Other suitable fiber sources or byproducts include, but are not limited to, rice hull fiber, rice bran fiber, oat hull fiber, beet pulp, sunflower hull fiber, corn hull fiber, and soy cotyledon fiber. The blend is dried, for example, as it quickly passes through a series of heated locks under pressure. The blend is then sprayed into a collection apparatus. Optionally, the extruded stabilized pancreas product may be further dried with coolers and/or evaporation conveyers.

In another embodiment, stabilized pancreas products of the invention are produced by spray drying. Any spray dryer known in the art may be used, including spray dryers with nozzles such as rotary atomizers and two fluid atomizers. In one embodiment, emulsified pancreas with from about 5 percent to about 50 percent dry matter is used in the spray drying production process. Powdered flow-aids may be optionally added to the emulsified pancreas to improve the spray-dry process. During this production process, emulsified pancreas may be heated to a liquid holding temperature from about 50 degrees Celsius to about 80 degrees Celsius, depending on the amount of dry matter in the emulsified pancreas. The emulsified pancreas may be forced under pressure through an atomizing nozzle into a drying chamber. Stabilized pancreas product then is collected from the drying chamber. The resulting stabilized pancreas product may comprise from about 80 percent to about 100 percent dry matter.

In yet another embodiment, stabilized pancreas products are produced by blending with an acidifier to achieve stabilization microbiologically and enzymatically. In accordance with this production method, pancreas glands, or optionally emulsified pancreas, may be blended with a suitable fiber source or byproduct, such as the soy hulls, or other plant fiber sources described above. The blend is stabilized with an acidifier that lowers the mixture pH to a range of between either about 7.5 to about 3.5, about 7.0 to about 4.0, about 6.5 to about 4.0, or about 6 to about 4.5. Propionic acid is an exemplary acidifier, and a wide variety of inorganic and organic acids, including acetic acid, may be used. This pH stabilization process produces a stabilized pancreas product with a range of dry matter content from about 5 percent to about 95 percent. Surprisingly, this pH stabilized pancreas product is exceptionally resistant to enzyme degradative hydrolysis, resistant to microbial and fungal spoilage, and resistant to fat oxidation. As such, a wet pH stabilized pancreas product may be stored and used similar to a forage, e.g. as silage of haylage.

The stabilized pancreas products of the invention are ready to use as feed additives. However, the stabilized pancreas products may be further processed by various means known to those skilled in the art.

In other embodiments, the stabilized pancreas products of the invention comprise from about 5 percent dry matter to about 95 percent dry matter. In some embodiments, dry stabilized pancreas products may comprise from about 70 percent to about 95 percent dry matter. In other embodiments, wet stabilized pancreas products may comprise from about 5 percent to about 30 percent dry matter.

In another embodiment, the stabilized pancreas products may be in the form of a mixed feed mash or as a top dressing. Alternatively, the stabilized pancreas products may be a dry powder. In one embodiment, the stabilized pancreas product is a dry powder containing less than about 20 percent moisture.

Moreover, the stabilized pancreas products of the invention may be further processed and used as a component of a formulated feed ration.

Use of Stabilized Pancreas Product

Another embodiment of the invention provides a feed additive comprising the stabilized pancreas product. In one embodiment, the feed additive is mixed or formulated to form a complete feed ration which is orally administered to the animal. In another embodiment, the feed additive is mixed or formulated with one or more components of a free-choice diet. In yet another embodiment, the feed additive is applied to the feed ration, for example, (1) by thorough mixing prior to feeding, (2) by spraying onto feed ration using devices such as spray applicators, or (3) as a top-dressing on a feed ration. In another embodiment, the feed additive is administered in conjunction with the administration of feed supplements, e.g. mineral blocks.

In another embodiment, a feed ration comprising a stabilized pancreas product may be of solid or liquid form. An exemplary solid feed ration may be formulated to contain about 0.1 percent (w/w) stabilized pancreas product feed additive. In other embodiments, solid feed rations may be formulated to contain from about 0.001 percent to about 1 percent stabilized pancreas product feed additive. An exemplary liquid feed ration may be formulated to contain about 0.1 percent (w/w) stabilized pancreas product feed additive. In other embodiments, liquid feed rations may be formulated to contain from about 0.001 percent to about 1 percent stabilized pancreas product feed additive.

The feed ration may be prepared from a wide range of dietary ingredients. For example, those skilled in the art recognize that a feed ration's energy component may be based on grains and their byproducts, such as corn, sorghum, oats, barley, wheat, and rye. Likewise, a feed ration's protein component may be based on either animal or plant protein, such as heat-treated whole soybeans, spray dried plasma protein, and dried skim milk or whey. A feed ration's lipid component may be obtained from sources of feed grade fats and oils, including animal (grease, tallow), vegetable (corn oil and soy oil) and restaurant and processing byproducts (blends of fats and oils). A feed ration may also contain forage and nonforage fiber sources and/or their respective byproducts. In addition, the feed ration may be balanced using feed supplements, such as vitamins and minerals. The feed ration may include other components according to the dietary nutritional and/or medical needs of the animal. Feed rations of the present invention may be prepared by any method known in the art, such as grinding or rolling, pelleting, and/or heat processing.

In one embodiment, the feed ration is formed into pellets. See, for example, U.S. Pat. No. 4,183,675 ("Energy conserving method and apparatus for pelleting particulate animal feed"). In brief, pellets may be formed by batching, mixing and pelleting steps carried out in known commercial equipment. This equipment may be combined in an installation consisting of a mixer which discharges into a surge bin, which in turn discharges into a pellet mill consisting of a variable-speed feeder, a steam conditioning chamber, and a die/roller assembly. Mash flows from the feeder through the conditioner, which discharges into the die/roller assembly where the stabilized pancreas product is extruded to form pellets. The pellets are then discharged from the pellet roll. A steam conditioning chamber is not essential to this exemplary process and may be optionally omitted.

Production Changes

In one embodiment, the present invention provides methods of using a stabilized pancreas product as a feed additive before, during, or after any period of production change. As used herein, "production change" is a term known in the art to denote a change from one feed to another or a change in environment. Production changes may be associated with the animal's life stage such as weaning from the dam, the onset and duration of pregnancy, or the accelerated finishing of animals. In another embodiment, stabilized pancreas product is used as a feed additive during times of production change caused by other factors, such as environmental factors. Environmental factors may include changes in the temperature or climate to which an animal is exposed, changes in the animal's housing, and changes in the animal's social group.

In other embodiments, stabilized pancreas product is used as a feed additive before, during, or after a production change that occurs during a transition from one food source to another, such as occurs, for example, when a new lot of ration is used, when the relative quantity and/or type of ration components is changed, when an animal is fed a ration that is mixed or formulated using different food sources than the previous ration, or in any change from one feed ration to a different feed ration.

In another embodiment, a stabilized pancreas product is used before, during, or after a period of production change in an animal undergoing a period of compensatory growth. A period of compensatory growth follows a period of feed nutrient restriction in most animals, and may be referred to by those skilled in the art as a grow-out cycle.

Another embodiment of the invention relates to methods of using a stabilized pancreas product to augment an animal's endogenous production of pancreatic enzymes. Methods of the invention are useful during periods of production change wherein pancreatic enzyme production is not sufficient to meet demands set by substrate quantity in the small intestine.

As used herein, "before a production change" denotes hours to days prior to the production change. In one embodiment, the invention relates to methods of using a stabilized pancreas product from about 1 hour to about 5 hours, up to about 1 day, before a production change. In another embodiment, the invention relates to methods of using a stabilized pancreas product from about 1 day to about 2 days, up to about 1 week, before a production change. In a third embodiment, the invention relates to methods of using a stabilized pancreas product beginning about 1 week or longer prior to the production change.

As used herein, "during a production change" refers to the hours and days over which a production change may occur. It refers to a variable length of time that begins with the a production change and may extend for hours and days depending on the nature and quality of the production change. For instance, this may occur over the course of hours where an animal is exposed to changes in the ambient temperature, or days if the animal is being transported long distances. In another embodiment, this may occur in a day where an animal is subjected to a transition from one food source to another food source. Other lengths of time may be apparent to those skilled in the art based on the nature and quality of the production change.

As used herein, "after a production change" refers to the hours and days subsequent to the production change. In one embodiment, the invention relates to methods of using stabilized pancreas from about 1 day to about 2 days, up to about 1 week, after a production change. In another embodiment, the invention relates to methods of using a stabilized pancreas product from about 1 week to about 2 weeks, or longer, after a production change.

The methods of using a stabilized pancreas product of the invention may be practiced on any animal that possesses a pancreas or produces digestive enzymes. The methods of the invention relate to any animal that produces digestive enzymes of the classes of enzymes normally excreted by the pancreas (i.e. proteases, amylases, lipases). Specific embodiments of the invention relate to production changes in cat, cattle, deer, dog, fish, goat, horse, llama, pig, poultry, rabbit, and sheep.

The invention also includes methods of using stabilized pancreas product at production changes specific to a given agricultural industry. For example, different agricultural industries may have specific periods of production change based upon the past, current, and future production methods of the industries. Examples are set forth below.

Aquaculture.

One production change in the aquaculture industry occurs when the fish gut matures to full functionality. Other production changes may include, but are not limited to, major temperature and aeration changes of the surrounding water.

The stabilized pancreas product of the present invention is suitable for use in aquaculture feed rations whereas prior products were not because activated pancreatic enzymes in the prior art products undergo autolysis quickly once exposed to water. Thus, the present invention provides a ration comprising stabilized pancreas product that is suitable for administration to fish and other aquatic animals. In one embodiment, the stabilized pancreas product comprises pancreatic enzymes in their zymogen form. In another embodiment, the stabilized pancreas product is sufficiently stable when immersed in water so as to avoid dissolution and autolysis of the enzymes.

Cattle.

In cattle, periods of production change may include, but are not limited to, the transition from milk to solid feed in calves; the transition from feed rations containing high proportions of forage and low proportions of concentrate to feed rations containing low proportions of forage and high proportions of concentrate; the transition to feed rations containing high levels of starch; and the transition from pasture to feed rations containing high levels of grain in cattle undergoing feedlot finishing.

Deer.

Periods of production change in deer, such as axis, fallow, red and silka deer and elk, include the transition from milk to solid feed in calves Horses.

In horses, production changes due to changes in diet, such as the transition from one feed source or ration to a different food source or ration, is particularly frequent as horses often change from a hay-based diet to a pasture-based diet. Likewise, a production change occurs when a horse transitions from one grain-based supplement to another grain-based supplement. Additionally, a period of production changes occurs during a period of stress in which digestive function is insufficient to prevent the passage of starch into the large intestine and cecum.

Pig.

In swine, periods of production change may include, but are not limited to, the postweaning transition period, flushing, gestation, the onset of lactation in sows, and accelerated finishing phase in growing-finishing pigs.

Poultry.

In poultry, a particularly crucial period of production change occurs as chicks are exposed to dry feed for the first time after birth. Other periods of production change include, but are not limited to, periods of molting in laying hens, and accelerated finishing in broilers and turkeys.

The stabilized pancreas product may be used as a feed additive during or after periods of production change, and/or before the onset of such periods in anticipation thereof. The prospective use of the stabilized pancreas product may prevent complications arising from periods of production change or from the natural consequences of any change in an animal's diet.

In one embodiment, stabilized pancreas product is mixed with a food source, such as milk replacer and/or starter feed, for young cattle in order to prevent the onset of scours or other natural consequences of transitioning from maternal milk to a solid feed ration. In another embodiment, stabilized pancreas product is mixed with the feed rations of companion animals, such as cats and dogs, to prevent or ameliorate the natural consequences of their diet and habits. In one embodiment, cats are fed a ration comprising stabilized pancreas product to prevent or ameliorate the accumulation of hairballs or gastric and intestinal trichobezoars.

EXAMPLES

The following examples are illustrative of the present invention and are not intended to be limitations thereon.

Example 1

Pancreas Glands

Porcine pancreas glands are obtained from the offal of abattoirs, slaughterhouses or a similar facility. The pancreas glands may be stored refrigerated or immediately emulsified. The glands are then emulsified using a plate grinder with water such that the emulsified pancreas contains approximately 25 percent dry matter. Optionally, fresh pancreas glands may be frozen and ground at a latter time.

Example 2

Extrusion

A stabilized pancreas product was produced by extrusion. Emulsified pancreas was blended with prepared soy hulls to a proportion of 35 percent emulsified pancreas to 65 percent soy hulls. The blend was forced through an extruder apparatus consisting of a series of steam locks with a metal surface temperature of 300 degrees Celsius. The blend passed through the apparatus in approximately 20 seconds and was sprayed into a collection apparatus.

Example 3

Spray Drying

A stabilized pancreas product was produced by spray drying. Emulsified pancreas containing approximately 62 percent moisture was fed through a number of heated atomizing nozzles mounted in a spinning drying chamber. Heated air was simultaneously fed to the drying chamber. The atomized pancreas product was dropped to the floor of the drying chamber where it was collected.

Example 4 pH Stabilization

A stabilized pancreas product was produced by a pH stabilization process. Emulsified pancreas was obtained with approximately 75 percent moisture content. Propionic acid was added to the emulsified pancreas until a pH of 4.5 was achieved. After the addition of the acid, the stabilized pancreas product turned gray and possessed a slightly-flowable to rubber-like viscosity.

In another example, emulsified pancreas was obtained as above and blended with prepared soy hulls. The blended pancreas consisted of approximately 35 percent emulsified pancreas and 65 percent prepared soy hulls. Propionic acid was added at a rate of 10 pounds per ton to the emulsified pancreas blend until a pH of 4.5 was achieved.

Example 5

Aquaculture Formulation

A feed ration suitable for use in aquaculture may be formulated using the stabilized pancreas product.

An exemplary formulation for a shrimp ration is:

| Ingredient | Percent (w/w) of Formulation |
| --- | --- |
| Wheat Flour | 28.00 |
| Soy Bean Meal | 35.50 |
| Fish Meal | 20.00 |
| Squid Meal | 4.00 |
| Lecithin | 2.00 |
| Corn Gluten Meal | 6.00 |
| Fish Oil | 2.50 |
| Misc. Vitamins and Minerals | 1.00 |
| Binder | 0.90 |
| Stabilized Pancreas Product | 0.10 |

An exemplary formulation for a tilapia ration is:

| Ingredient | Percent (w/w) of Formulation |
| --- | --- |
| Wheat Flour | 27.00 |
| Soy Bean Meal | 35.00 |
| Corn | 5.90 |
| Rice Bran | 10.00 |
| Fish Meal | 12.00 |
| Misc. Vitamins and Minerals | 1.00 |
| Corn Gluten Meal | 9.00 |
| Stabilized Pancreas Product | 0.10 |

Example 6

Cattle Formulation

A feed ration suitable for use in cattle may be formulated using the stabilized pancreas product.

An exemplary formulation for a milk replacer comprising a stabilized pancreas product is:

| Ingredient | Percent (as-is) of Formulation |
| --- | --- |
| Whey Protein Concentrate | 33.00 |
| Dried Whey | 31.73 |
| Dry Fat (7.7% crude protein/60.3% crude fat) | 31.00 |
| Calcium Carbonate | 0.55 |
| Dicalcium Phosphate | 0.40 |
| Misc. Vitamins, Minerals, and Additives | 2.00 |
| Stabilized Pancreas Product | 0.32 |
| Amino Acids | 1.00 |

Example 7

Deer Formulation

A feed ration suitable for use in deer may be formulated using the stabilized pancreas product.

An exemplary formulation for a deer ration is:

| Ingredient | Percent (w/w) of Formulation |
| --- | --- |
| Fine Ground Corn | 0.60 |
| Wheat Midds | 30.00 |
| Soy Hulls | 15.00 |
| Malt Sprouts | 10.00 |
| Salt | 17.00 |
| Dehydrated Alfalfa | 3.00 |
| Calcium Carbonate | 3.00 |
| Distillers Grains with Solubles | 21.00 |
| Canola Meal | 0.25 |
| Trace Mineral | 0.05 |
| Stabilized Pancreas Product | 0.10 |

Example 8

Horse Formulation

A feed ration suitable for use in horses may be formulated using the stabilized pancreas product.

An exemplary formulation for an equine ration is:

| Ingredient | Percent (w/w) of Formulation |
| --- | --- |
| Ground Corn | 11.00 |
| Ground Oats | 23.00 |
| Wheat Midds | 30.55 |
| Soy Bean Meal | 0.25 |
| Salt | 0.60 |
| Dehydrated Alfalfa | 4.00 |
| Calcium Carbonate | 2.40 |
| Distillers Grains with Solubles | 20.00 |
| Oil | 2.50 |
| Misc. Vitamins, Minerals, and Additives | 5.25 |
| Stabilized Pancreas Product | 0.10 |
| Amino Acids | 0.35 |

Example 9

Poultry Formulation

A feed ration suitable for use in poultry may be formulated using the stabilized pancreas product.

An exemplary formulation for a domesticated turkey ration is:

| Ingredient | Percent (w/w) of Formulation |
| --- | --- |
| Finely Ground Corn | 53.71 |
| Wheat Midds | 11.54 |
| Meat and Bone Meal | 8.00 |
| Feather Meal | 5.00 |
| Malt Sprouts | 10.00 |
| Soy Bean Meal | 6.40 |
| Salt | 0.15 |
| Calcium Carbonate | 0.44 |
| Cereal Fines | 4.10 |
| Misc. Vitamins, Minerals, and Additives | 0.42 |
| Stabilized Pancreas Product | 0.10 |
| Amino Acids | 0.14 |

Example 10

Pig Formulation

A feed ration suitable for use in swine may be formulated using the stabilized pancreas product.

An exemplary formulation for a swine ration is:

| Ingredient | Percent (w/w) of Formulation |
| --- | --- |
| Ground Corn | 40.53 |
| Dried Whey | 25.00 |
| Soy Bean Meal | 22.00 |
| Salt | 0.05 |
| Fat | 5.00 |
| Calcium Carbonate | 0.22 |
| Dicalcium Phosphate | 0.90 |
| Animal Protein Products | 5.50 |
| Misc. Vitamins, Minerals, and Additives | 0.70 |
| Stabilized Pancreas Product | 0.10 |

Example 11

Enzyme Levels in Stabilized Pancreas Product

This example compares the enzymatic activity of various preparations of stabilized pancreas product.

The moisture content, protease activity, and amylase activity were determined for spray-dried, freeze-dried, extruded, and pH stabilized pancreas products. Table 1 sets forth the various protease and amylase activity levels of stabilized pancreas products of the present invention. For each preparation, the enzyme activity of pancreatin is used as a comparative baseline.

In Table 1, "spray dried" refers to the procedure described in Example 3; "freeze dried" refers to lyophilized pancreas glands prepared by methods known in the art; "extrusion" refers to the procedure described in Example 2 and "pH stabilized" refers to stabilized pancreas product blended with a carrier of soy hulls as described in Example 4.

All samples were stored under the conditions indicated in Table 1 for 6 days.

For each preparation, 1 part stabilized pancreas product was mixed with 4 parts of mature pig small intestinal content at room temperature for 2 minutes. Aliquots of each preparation were diluted and examined to determine protease activity levels.

Protease activity levels were determined as follows. For samples with less than approximately 1000 U/G, 10 g of samples were mixed in about 80 mL of 2 percent sodium chloride solution for approximately 30 minutes. The solution volume was increased to 100 mL with 2 percent sodium chloride solution and filtered through glass fiber filter paper *GLASS MICROFIBRE GF/A*, Whatman plc, Florham Park, N.J.). 1 mL of sample solution and reagents were equilibrated at 40 degrees Celsius. 5 mL of 0.6 percent (w/v) casein substrate (Hammarten Casein, Merck & Co., Inc., Whitehouse Station, N.J.) was added to each sample and incubated at 40 degrees Celsius for about 30 minutes. 5 mL of precipitation reagent (18.8 g of trichloroacetic acid, 18.1 g of anhydrous sodium acetate, and 18.8 g of acetic acid in distilled water to a volume of 1000 mL) was added. Samples were then incubated at 40 degrees Celsius for about 30 minutes. Samples were immediately filtered through laboratory qualitative filter paper (Whatman Grade 1, Whatman plc, Florham Park, N.J.), cooled to room temperature and measured for absorbance at 660 nm. Sample absorbances were measured against enzyme blanks and a standard curve of tyrosine solutions liberated by Folin-Ciocalteau phenol reagent.

α-amylase activity levels were determined as follows. Reagent solution (9 g sodium chloride, 2 g bovine serum albumin, and 2.2 g of calcium chloride in distilled water to a volume of 1000 mL) and 0.5 M sodium hydroxide solution were prepared. Samples were prepared by dilution into 204 mL of reagent solution, and equilibrated to 37 degrees Celsius. A substrate PHADEBAS® Amylase Test Tablet (Pharmacia Diagnostics, Uppsala, Sweden) was added to each sample, and mixed vigorously for 10 seconds. Samples were then incubated for 15 minutes. 1 mL of 0.5 M sodium peroxide solution was added, and the solution was immediately centrifuged at 3500 rpm for 10 minutes. Sample absorbance was measured at 620 nm against a reagent blank, and α-amylase activity was determined according to the manufacturer's instructions.

over a period of 6 days. Such results exemplify the stability of the products of the invention.

Example 12

Feed Trial in Weanling Pigs

In this example, a feed trial was conducted to investigate the efficacy of the freeze-dried pancreas at reducing post weanling-lag in pigs. Six treatment groups were fed rations containing (1) no pancreatin or stabilized pancreas product; (2), 0.1 percent (w/w) pancreatin; (3) 0.2 percent (w/w) pancreatin; (4) 0.1 percent stabilized pancreas product, (5) 0.2 percent stabilized pancreas product, and (6) 0.4 percent stabilized pancreas product. Data were analyzed as a randomized complete block design by the GLM procedure (SAS Institute Inc., Cary, N.C.).

As shown in Table 2, the freeze-dried pancreas exhibits a positive, quadratic effect on both feed intake and weight gain

TABLE 1

Enzyme Levels in Stabilized Pancreas Products

| Sample | Storage | Moisture | Protease (Dry Matter Basis) | | Amylase (Dry matter Basis) | |
|---|---|---|---|---|---|---|
| | | | U/g | Percent Activity | U/g | Percent Activity |
| Pancreatin | −20° C. | 3.60 | 414, 243 | 100 | 18,174 | 100 |
| Freeze-Dried #1 | −80° C. | 4.68 | 335, 742 | 81 | 19,167 | 105 |
| Freeze-Dried #2 | 4° C. | 4.92 | 387, 137 | 93 | 19,215 | 106 |
| *Freeze-Dried Blended with Soy Hulls | −80° C. | 6.32 | 732, 891 | 177 | 14,854 | 82 |
| *pH stabilized | Ambient Temperature | 25.27 | 856, 423 | 207 | 13,932 | 77 |
| *Extruded | Ambient Temperature | 16.57 | 545, 334 | 132 | 603 | 3 |
| Spray-Dried | Ambient Temperature | 1.98 | 138, 987 | 34 | 33 | 0 |

*Protein contained in blended soy hulls was not accounted for, thus, protease activity may exceed that of the pancreatin.

Accordingly, the stabilized pancreas products shown in Table 1 retain similar, if not superior, protease activity levels as compared to pancreatin. In addition, the stabilized pancreas products shown in Table 1 retain similar, or reduced, amylase activity levels as compared to pancreatin. These results are particularly surprising considering the storage of the stabilized pancreas products at ambient temperatures during the first week postweaning. Both of these measures increase with the percent of freeze-dried pancreas in the diet. In a ration containing 0.2 percent freeze-dried pancreas, feed intake is improved by 31 percent and weight gain is improved by 83 percent. As shown in Table 3, freeze-dried pancreas has no effect on these measures during the subsequent two weeks.

TABLE 2

Reduction of Post-Weaning Lag in Pigs During Week 1

| | Treatment | | | | | | | P-Values | | | |
|---|---|---|---|---|---|---|---|---|---|---|---|
| | 1 | 2 | 3 | 4 | 5 | 6 | | Pancreatin | | Pancreas | |
| Pancreatin (percent) | 0.00 | 0.10 | 0.20 | 0.00 | 0.00 | 0.00 | | | | | |
| Freeze-Dried (percent) | 0.00 | 0.00 | 0.00 | 0.10 | 0.20 | 0.40 | SEM | Linear | Quadratic | Linear | Quadratic |
| Feed Intake (lbs/day) | 0.32 | 0.40 | 0.29 | 0.45 | 0.42 | 0.38 | 0.058 | 0.735 | 0.253 | 0.568 | 0.117 |
| Weight Gain (lbs/day) | 0.12 | 0.22 | 0.15 | 0.18 | 0.22 | 0.17 | 0.040 | 0.626 | 0.106 | 0.256 | 0.166 |
| Feed:Gain (Ratio) | 4.26 | 2.19 | 3.50 | 2.97 | 2.49 | 2.69 | 0.808 | 0.513 | 0.107 | 0.224 | 0.377 |

TABLE 3

Reduction of Post-Weaning Lag in Pigs During Weeks 2–3

| | Treatment | | | | | | | P-Values | | | |
|---|---|---|---|---|---|---|---|---|---|---|---|
| | 1 | 2 | 3 | 4 | 5 | 6 | | Pancreatin | | Pancreas | |
| Pancreatin (percent) | 0.00 | 0.10 | 0.20 | 0.00 | 0.00 | 0.00 | | | | | |
| Freeze-Dried (percent) | 0.00 | 0.00 | 0.00 | 0.10 | 0.20 | 0.40 | SEM | Linear | Quadratic | Linear | Quadratic |
| Feed Intake (lbs/day) | 0.91 | 0.89 | 0.76 | 0.92 | 0.97 | 0.90 | 0.72 | 0.165 | 0.559 | 0.980 | 0.542 |
| Weight Gain (lbs/day) | 0.72 | 0.68 | 0.70 | 0.73 | 0.77 | 0.77 | 0.058 | 0.769 | 0.721 | 0.460 | 0.950 |
| Feed:Gain (Ratio) | 1.29 | 1.32 | 1.11 | 1.30 | 1.29 | 1.16 | 0.082 | 0.153 | 0.297 | 0.264 | 0.357 |

All publications, patents and patent applications identified above are herein incorporated by reference.

The invention being thus described, it will be apparent to those skilled in the art that the same may be varied in many ways without departing from the spirit and scope of the invention. Such variations are included within the scope of the invention to be claimed.

What is claimed is:

1. A stabilized pancreas product comprising an emulsification of whole pancreas, blended with soy hulls,
   wherein said emulsification comprises one or more pancreatic enzymes in zymogen form, at least one of which is a protease;
   wherein said pancreas is not defatted; and
   wherein said product is stable upon exposure to air and water.

2. The stabilized pancreas product according to claim 1, wherein said product contains about 1 percent to about 20 percent moisture.

3. The stabilized pancreas product according to claim 1, wherein said product contains about 20 percent to about 95 percent moisture.

4. The stabilized pancreas product of claim 1, wherein said product, when activated, has an amylase activity of at least about 0 percent of the amylase activity of pancreatin.

5. The stabilized pancreas product of claim 1, wherein said product, when activated, has an amylase activity of at least about 3 percent of the amylase activity of pancreatin.

6. The stabilized pancreas product of claim 1, wherein said product, when activated, has an amylase activity of at least about 75 percent of the amylase activity of pancreatin.

7. The stabilized pancreas product of claim 1, wherein said product, when activated, has an amylase activity of at least about 105 percent of the amylase activity of pancreatin.

8. The stabilized pancreas product of claim 1, wherein said product, when activated, has a protease activity of at least about 25 percent of the protease activity of pancreatin.

9. The stabilized pancreas product of claim 1, wherein said product, when activated, has a protease activity of at least about 80 percent of the protease activity of pancreatin.

10. The stabilized pancreas product of claim 1, wherein said product, when activated, has a protease activity of at least about 100 percent of the protease activity of pancreatin.

11. The stabilized pancreas product of claim 1, wherein said product, when activated, has a protease activity of at least about 130 percent of the protease activity of pancreatin.

12. The stabilized pancreas product of claim 1, wherein said product, when activated, has a protease activity of at least about 200 percent of the protease activity of pancreatin.

13. A feed additive comprising a stabilized pancreas product as recited in claim 1.

14. An animal feed ration comprising a feed additive as recited in claim 13.

15. The animal feed ration of claim 14, wherein the feed additive is about 0.1 percent (w/w) of the feed ration.

16. The animal feed ration of claim 14, wherein the feed additive is about 0.2 percent (w/w) of the feed ration.

17. The animal feed ration of claim 14, wherein the feed additive is about 0.4 percent (w/w) of the feed ration.

18. The animal feed ration of claim 14, wherein the feed additive is about 0.5 percent (w/w) of the feed ration.

19. The animal feed ration of claim 14, wherein said ration is formulated for an animal selected from the group consisting of cat, cattle, deer, dog, fish, goat, horse, llama, pig, poultry, rabbit, and sheep.

20. The stabilized pancreas product of claim 1, comprising trypsin in its zymogen form.

21. The stabilized pancreas product of claim 1, comprising chymotrypsin in its zymogen form.

22. The composition of claim 1, further comprising an acidifier, wherein the pH of the product is between about 4.5 and about 6.0.

23. A method comprising orally administering the stabilized pancreas product of claim 1 to an animal.

24. The method of claim 23, wherein said stabilized pancreas product is administered to an animal beginning from about 1 week prior to a production change to about 1 week after the production change.

25. The method of claim 24, wherein the production change is a transition from a first food source to a second food source.

26. The method of claim 24, wherein the production change is a transition from a liquid food source to a solid food source.

27. The method of claim 24, wherein the production change is weaning from a dam.

28. The method of claim 23, wherein said ration is formulated for an animal selected from the group consisting of cat, cattle, deer, dog, fish, goat, horse, llama, pig, poultry, rabbit, and sheep.

29. A method of making a stabilized pancreas product comprising the steps of:
   emulsifying one or more whole pancreas glands to yield emulsified pancreas; and
   blending the emulsified pancreas with soy hulls to yield a stabilized pancreas product,
   wherein said method does not comprise the removal of fats from said one or more whole pancreas glands, and wherein said product is stable upon exposure to air and water.

30. The method of claim 29, wherein the acidifier is selected from the group consisting of propionic acid, acetic acid, and a combination thereof.

31. The method of claim 29, wherein the emulsified pancreas is acidified to a pH of about 6.0 to about 4.5.

32. The method of claim 29, further comprising a step of blending the emulsified pancreas glands and soy hulls with an acidifier.

33. A method of making a stabilized pancreas product comprising the steps of:
   emulsifying one or more whole pancreas glands to yield emulsified pancreas;
   mixing the emulsified pancreas with soy hulls; and
   extruding the resulting mixture to yield a stabilized pancreas product,
   wherein said method does not comprise the removal of fats from said whole pancreas glands, and
   wherein said product is stable upon exposure to air and water.

34. The method of claim 33, further comprising the step of drying the stabilized pancreas product in at least one apparatus selected from the group consisting of a cooler and an evaporation conveyer.

35. A method of making a feed ration comprising the steps of:
   providing a range of dietary ingredients; and
   mixing the ingredients with a stabilized pancreas product of claim 1, thereby obtaining a feed ration comprising a stabilized pancreas product.

36. The method of claim 35, further comprising the step of forming the feed ration into pellets.

* * * * *